(12) United States Patent
McGrath et al.

(10) Patent No.: US 11,896,197 B2
(45) Date of Patent: Feb. 13, 2024

(54) ELECTRICAL DEVICE POWER MANAGEMENT

(71) Applicant: Covidien AG, Neuhausen am Rheinfall (CH)

(72) Inventors: Matthew John Ross McGrath, Edinburgh (GB); Peter Douglas Colin Inglis, Edinburgh (GB); Brian Alan Laffoley, Edinburgh (GB)

(73) Assignee: Covidien AG (CH)

( * ) Notice: Subject to any disclaimer, the term of this patent is extended or adjusted under 35 U.S.C. 154(b) by 201 days.

(21) Appl. No.: 17/356,074

(22) Filed: Jun. 23, 2021

(65) Prior Publication Data

US 2021/0318382 A1  Oct. 14, 2021

Related U.S. Application Data

(60) Continuation of application No. 16/289,141, filed on Feb. 28, 2019, now Pat. No. 11,073,562, which is a
(Continued)

(51) Int. Cl.
| | | |
|---|---|---|
| A61B 1/00 | (2006.01) | |
| G01R 31/382 | (2019.01) | |
| A61B 1/267 | (2006.01) | |
| H01M 6/50 | (2006.01) | |
| H01M 10/48 | (2006.01) | |
| H01M 50/24 | (2021.01) | |
| H01M 50/209 | (2021.01) | |

(Continued)

(52) U.S. Cl.
CPC ...... *A61B 1/00034* (2013.01); *A61B 1/00025* (2013.01); *A61B 1/04* (2013.01); *A61B 1/267* (2013.01); *G01R 31/3648* (2013.01); *G01R 31/382* (2019.01); *H01M 6/50* (2013.01); *H01M 10/48* (2013.01); *H01M 10/488* (2013.01); *H01M 50/209* (2021.01); *H01M 50/24* (2021.01); *A61B 1/00029* (2013.01); *H01M 6/5044* (2013.01); *H02J 7/0048* (2020.01)

(58) Field of Classification Search
CPC ... A61B 1/00025; A61B 1/00034; A61B 1/04; A61B 1/267
See application file for complete search history.

(56) References Cited

U.S. PATENT DOCUMENTS

| | | |
|---|---|---|
| 5,654,623 A | 8/1997 | Masaaki et al. |
| 6,236,214 B1 | 5/2001 | Camp et al. |

(Continued)

FOREIGN PATENT DOCUMENTS

JP       11023678 A      1/1999

OTHER PUBLICATIONS

International Search Report for PCT/GB2011/050926, dated Nov. 2, 2011, 5 pages.

*Primary Examiner* — Sameh R Boles

(57) ABSTRACT

An electrical device includes a memory storing a value indicative the remaining available rated capacity of one or more batteries. The stored value is changed in use to reflect reducing capacity. The initial stored value is chosen so that there is a very high (e.g. >99.9%) confidence that the one or more batteries will provide at least the capacity indicated by the initial stored value. This reduces the chance of failure during emergency procedures. The one or more batteries may be integral to the electrical device. An override facility is provided.

14 Claims, 6 Drawing Sheets

Related U.S. Application Data division of application No. 15/881,457, filed on Jan. 26, 2018, now Pat. No. 10,261,135, which is a continuation of application No. 15/097,005, filed on Apr. 12, 2016, now Pat. No. 9,880,227, which is a continuation of application No. 14/721,123, filed on May 26, 2015, now Pat. No. 9,316,698, which is a continuation of application No. 13/697,660, filed as application No. PCT/GB2011/050926 on May 13, 2011, now Pat. No. 9,066,668.

(51) Int. Cl.
  *A61B 1/04* (2006.01)
  *G01R 31/36* (2020.01)
  *H02J 7/00* (2006.01)

(56) References Cited

U.S. PATENT DOCUMENTS

| | | |
|---|---|---|
| 9,066,668 B2 | 6/2015 | McGrath et al. |
| 2003/0193314 A1* | 10/2003 | Solingen .............. A61B 5/0059 320/107 |
| 2004/0098222 A1 | 5/2004 | Pehrsson et al. |
| 2007/0106121 A1 | 5/2007 | Yokota et al. |
| 2013/0066153 A1 | 3/2013 | McGrath et al. |

\* cited by examiner

ELECTRICAL DEVICE POWER MANAGEMENT

CROSS REFERENCE TO RELATED APPLICATIONS

This application is a continuation of application Ser. No. 16/289,141, filed on Feb. 28, 2019, which is a divisional of U.S. Pat. No. 10,261,135, filed on Jan. 26, 2018, which is a continuation of U.S. Pat. No. 9,880,227, filed Apr. 12, 2016, which is a continuation of U.S. Pat. No. 9,316,698, filed May 26, 2015, which is a continuation application of U.S. Pat. No. 9,066,668, filed Nov. 13, 2012, which is the National Phase of International Application No. PCT/GB2011/050926, filed 13 May 2011, which designated the U.S. and claims priority to GB Application No. 1008020.8, filed 13 May 2010, and GB Application No. 1017292.2, filed 13 Oct. 2010, the entire contents of each of which are hereby incorporated by reference for all purposes.

FIELD OF THE INVENTION

The invention relates to electrical devices, including electrical medical devices, which are powered by batteries and which are operated in environments where they may come into contact with liquid.

BACKGROUND TO THE INVENTION

Electrical devices, such as electrical medical devices, may incorporate a battery power supply to enable them to be used without the limitations of a power cable.

A known problem with battery powered electrical devices, including electrical medical devices such as laryngoscopes, is that the batteries may be depleted and the power supply may fail during use. The battery compartments of such devices will typically receive any of a wide range of batteries having a similar external shape but substantially different electrical properties and capacities. Furthermore, it may not be apparent if a battery has been used before. Thus, it may not be possible to predict exactly when the power supply may fail. Thus, in many known devices, there is a substantial risk of a failure in the power supply during use. This is of particular concern in relation to electrical medical devices, such as laryngoscopes, which may be used in emergency procedures. This risk of a failure in the power supply can be reduced by using new batteries for each procedure. However, this is very wasteful.

Accordingly, some aspects of the invention aim to provide improved methods of minimising the risk of the battery power supply of an electrical device failing during a procedure.

Furthermore, many such electrical devices may be used in environments where they may come into contact with liquid. For example, electrical medical device for in vivo use may be used in environments where they come into contact with bodily fluids and electrical medical devices which include reusable portions requiring decontamination between uses may be used in environments where they come into contact with cleaning products.

It is often necessary for such electrical devices to be sealed against penetration by liquid to prevent damage to the device or loss of battery power.

A secondary concern is to avoid gaps leading to spaces where microbes can proliferate, and which can be prove difficult to clean.

Thus, the aim of some embodiments of the invention is to provide an electrical device (for example, an electrical medical device such as a laryngoscope) which is reliably sealed against penetration by liquid.

SUMMARY OF THE INVENTION

According to a first aspect of the invention there is provided an electrical device comprising an electrical device body, one or more batteries and a memory storing a value indicative of the remaining available rated capacity of the one or more batteries, the electrical device comprising a usage recording device operable to determine when the electrical device is operated and to update the value stored in the memory responsive to such usage to reflect the consumption of power from the one or more batteries resulting from the said operation. The stored value is therefore the remaining available rated capacity value initially stored in the memory, updated by the actions of the usage recording device. After sufficient use the stored value will be indicative that the initial rated capacity of the one or more batteries has been consumed, for example, the stored value may be progressively reduced until it reaches a value, such as zero, indicative that the available rated capacity has been consumed.

By the rated capacity we refer to the amount of power which can be obtained from the one or more batteries, while the batteries have electrical properties (such as potential difference) sufficient to power normal operation of the electrical device, according to a predetermined (rated) specification of the amount of power which the one or more batteries should provide in a very high proportion of cases. The remaining available rated capacity is the amount of that rated capacity which has not yet been consumed as updated by the usage recording device during use.

The value of remaining available rated capacity initially stored in the memory is selected so that, in a very high proportion of cases, typically at least 99% and preferably at least 99.9% or at least 99.99% of cases, the one or more batteries will have remaining stored power which could be used to power normal operation of the electrical device when the stored value reaches a value indicative that the rated capacity has been exhausted. Thus, if the one or more batteries in aggregate are found to deliver 105.0 to 175.0 mAh in 99.9% of cases, taking into account the range of uses to which the electrical devices are put, the value initially stored in the memory well be set so that it is updated to a value indicative that the initial capacity has been consumed when at most 105.0 mAh have been used. As a result of this margin for error, if the stored value is indicative that an amount of capacity exceeding that required for a procedure remains stored in the one or more batteries, the user can have a very high confidence that the electrical device will continue to operate throughout the procedure, reducing the risk of failure which could otherwise occur in devices which enable a user to use any battery of a specific class which encompasses batteries having very different capacities (e.g. AA or AAA batteries, which have compositions and capacities which vary widely between brands and types, for example Alkaline, NiMH or Lithium).

The use of stored values which are updated when use occurs can provide a more accurate estimate of guaranteed remaining capacity than the use of measurements of remaining battery capacity, which can be unreliable, especially when the battery capacity is close to exhausted.

The one or more batteries may be provided in a battery pack comprising the one or more batteries. The battery pack may comprise the memory.

The usage recording device typically determines when use is occurring and transmits signals to the battery pack indicative that the value stored in the memory should be updated. The signals may represent an updated value to be written to the memory, or that the stored value should be changed by a certain amount, for example, incremented or decremented. The usage determining module may communicate wirelessly with the battery pack. For example, the memory may be part of an RFID tag located in the battery pack, read from and written to by a solenoid aerial in the body of the electrical device.

In some embodiments the electrical device comprises a removable battery pack comprising the one or more batteries and the memory. Thus, the removable battery pack includes a memory storing a value indicative of the remaining available capacity of the one or more batteries in the removable battery pack. The battery pack may lack a recharge interface. For example, the battery pack may lack an external power input.

However, in some embodiments, the one or more batteries (e.g. battery pack) is integral to the electrical device body such that the user may not remove the battery pack from the electrical device body. The one or more batteries (e.g. battery pack) may be mounted to (for example within) the electrical device body. The electrical device body (and the battery pack in embodiments where the battery pack defines at least part of the outer surface of the electrical device) may be covered with a sealing layer, for example of a fluid resistant material, such as silicon, to form a continuous surface around the electrical device, for example, around a handle of the electrical device. Therefore, the one or more batteries (e.g. battery pack) may be sealed from any potentially hazardous solvent, such as water or a non-aqueous solvent used for cleaning the electrical device, for example.

The sealing layer may allow the electrical device to be fully submersible, that is, electrical device may be fully submerged in water, for example, without suffering damage.

Preferably, the one or more batteries are disposable batteries. That is, the one or more batteries may not be recharged after the available rated capacity of the one or more batteries has been consumed. In some embodiments, the one or more batteries may be rechargeable batteries integral to the electrical device and the electrical device may lack an interface for recharging the batteries. Thus, the user cannot recharge the batteries, although a manufacturer or their agent might do so, after dismantling the electrical device. Alternatively, the manufacturer or their agent may recharge the one or more batteries wirelessly (for example, using a capacitive charger). Typically, the one or more batteries cannot be removed without breaking a part (e.g. a sealing layer). This avoids the risk of a user changing one or more batteries, or recharging them, leading to a situation where the amount of remaining power cannot be guaranteed and there is a risk of the electrical device failing during a procedure (e.g. failing during intubation in the case of a video laryngoscope).

Therefore, the electrical device must be replaced when the available rated capacity of the one or more batteries has been consumed.

Where the electrical device is only intended for infrequent use (for example, less than 20 applications a year) one or more integral batteries that may not be replaced or recharged in situ allows the electrical device to be thoroughly sealed with a continuous layer of material, providing a minimum number of features such as creases, within which contaminants such as bacteria, for example, may grow. In addition, the electrical device with one or more integral batteries allows for simplicity of construction, a lower cost of parts (as there may be fewer parts) and a higher reliability (as there may be fewer moving parts) than a similar electrical device with at least one removable battery, for example.

Alternatively, the electrical device may be intended for frequent use (for example, the one or more batteries may hold enough charge for 400 minutes of use, 800 minutes of use or more than 1000 minutes of use.

During the lifetime of rechargeable batteries, the maximum available rated capacity degrades as the battery is repeatedly recharged. In addition, the characteristics of the rate of change of the available rated capacity as the battery is used may be changed or degraded, resulting in inaccurate values of available rated capacity. Such inaccuracies could lead to failure of the device during use.

Accordingly, the use of disposable batteries ensures that the stored value of available rated capacity is accurate and dependable such that device failures during use, due to the batteries become depleted, are effectively eradicated.

It may be that the memory is a passive device such that power is only consumed by the memory when data is read from or written to the memory. Thus, where the memory is part of an RFID tag, the RFID tag is preferably a passive RFID tag.

The stored value may be numerical value representing remaining available rated capacity. The stored value for a new fully charged battery pack may have a predetermined integer value, such as 100, 256, 500 etc. which is progressively decremented by the memory updating module in use, and a battery which has output its rated amount of power would have a stored value of zero. The stored value may count up. The value may be stored in any form, for example, the memory may comprise a plurality of fuses or antifuses which are triggered in turn with the number of fuses or antifuses which have been triggered or which remain untriggered indicating the stored value.

The stored value may be indicative of a number of units of time, such as hours or minutes, of operating of the electrical device (optionally, in one or more modes) for which the battery pack has remaining available rated capacity for a given power consumption. This is especially helpful where the power consumption of the medical device is substantially constant in use. The stored value may be indicative of a number of procedures which the electrical device can carry out using the remaining available capacity (for example, intubation procedures where the electrical device is a video laryngoscope).

The electrical device may display an indicator of the amount of capacity remaining in the battery pack based on the stored value. The indicator may comprise a light source or a plurality of light sources. The plurality of light sources may comprise light sources which emit light of a different colour to each other. The electrical device may comprise a screen and the screen may display the indicator. For example, where the electrical device is a video laryngoscope having a screen, the screen may display the indicator. The indicator may be a number. The indicator may be a number representative of an amount of time, or a number of procedures which the electrical device can carry out using the remaining available capacity (for example, intubation procedures where the electrical device is a video laryngoscope).

The electrical device may comprise a loudspeaker and generate a sound indicative that the remaining capacity determined from the stored value is approaching zero.

The electrical device may stop, or not start, carrying out one or more operating functions once the remaining available rated capacity indicated by the stored value is below a threshold (for example, a few percent of maximum capacity, or zero, or a predetermined negative value). The electrical device may indicate one or more warning to a user before this occurs.

The electrical device may comprise an override to enable a user to continue to carry out, or to start, some or all of the operating functions even though this has occurred. The override may comprise a switch. The override may comprise a microphone and allow a user to continue to carry out, or to start, some or all of the operating functions responsive to a sufficiently loud sound detected by the microphone (e.g. the user shouting at the device from close range). This is advantageous as it allows a user to obtain additional function where required, but it dissuades a user (who would typically not wish to shout in certain environments) from using an override activated by a sufficiently loud sound. The override mechanism may comprise a switch, or another form of user input such as pressure sensors or sound sensors, for example.

Typically, an electrical device is an electrical medical device. The medical device may be a handheld medical device, such as an ultrasound scanner, infusion pump controller and infusion pump, diagnostic device, blood monitor, e.g. blood glucose monitor, endoscopes or other devices for probing within the human body.

The electrical device may be an intubation instrument such as a laryngoscope, preferably a video laryngoscope.

In embodiments where the electrical device is a laryngoscope, the laryngoscope may comprise a handle and an arm. The handle may comprise a first end adjacent to the arm, and an opposed second end. The one or more integral batteries may be located within the handle of the laryngoscope adjacent to the first end.

Preferably, the one or more batteries are located closer to the first end than the second end. Preferably, the centre of mass of the one or more batteries is located at least two-thirds, preferably three-quarters, of the way from the second end to the first end.

The majority of the electronics within the handle of the laryngoscope may be located closer to the first end than the second end, for example, at least two-thirds (or preferably three-quarters) of the way from the second end to the first end. They may be adjacent to the first end of the handle.

In embodiments where the electrical device is a laryngoscope and the laryngoscope body comprises a handle, the provision of the one or more batteries and/or the majority of the electronics located closer to the first end of the handle ensures that the centre of gravity of the handle is closer to the first end of the handle than the second end, and ensures that the laryngoscope handle is stabilised within the hand of a user. In addition, the provision of the one or more batteries and/or the majority of the electronics being located adjacent to the first end of the electrical device body ensures that the electronics are compact. The electronics may be mounted onto a printed circuit board (PCB). The one or more batteries may be mounted onto a PCB. Both the electronics and the one or more batteries may be mounted onto the PCB. The PCB may be located in the body. The PCB may be located in the arm. The PCB may extend from the body into the arm. The PCB may also function as a strengthening element to strengthen the arm.

The second end of the electrical device body may comprise a low density portion. The low density portion may comprise an air pocket. The low density portion may comprise a low density foam.

Alternatively, the low density portion may comprise a recess in the surface of the electrical device body. The recess may allow the user to grip the electrical device more securely.

Where the electrical device is a video laryngoscope, the laryngoscope may comprise a screen connected to the battery and electronics of the laryngoscope by a connector. The connector may be a physical wire. The connector may be an optical connection such as an optical fibre. The connector may be a wireless connector or transmitter.

According to a second aspect of the invention there is provided a laryngoscope comprising a handle comprising one or more integral batteries and a laryngoscope arm extending from the handle, the handle having a first end adjacent to the arm and an opposed second end; wherein the one or more batteries are closer to the first end than the second end.

DESCRIPTION OF THE DRAWINGS

An example embodiment of the present invention will now be illustrated with reference to the following Figures in which.

DETAILED DESCRIPTION OF EXAMPLE EMBODIMENTS

First Embodiment

Figure 1:
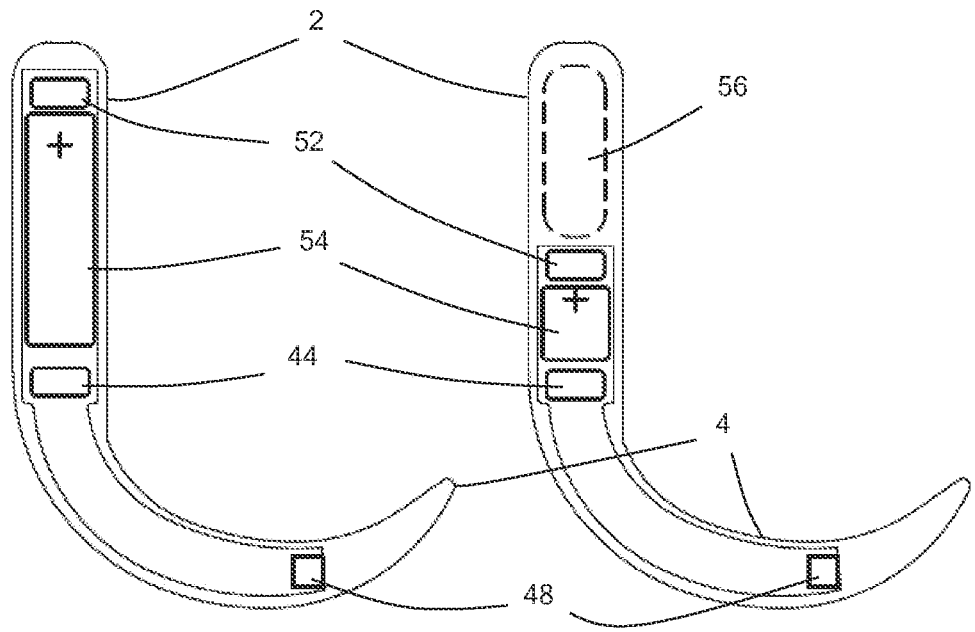
FIG. 1 is a series of side-on plan views of embodiments of video laryngoscopes.
Figure 1:
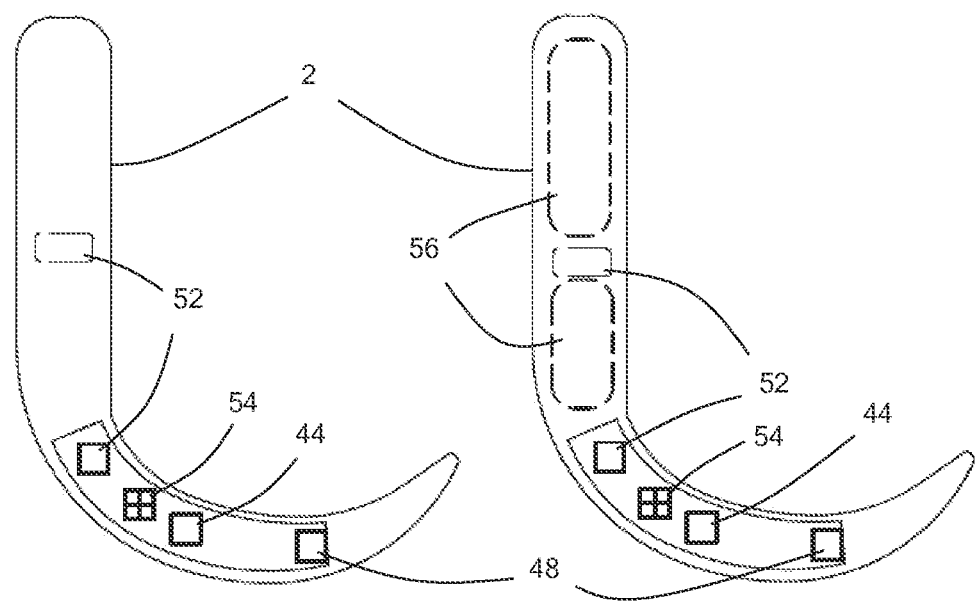
Figure 1:
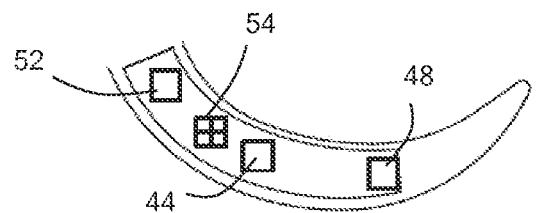
Figure 2:
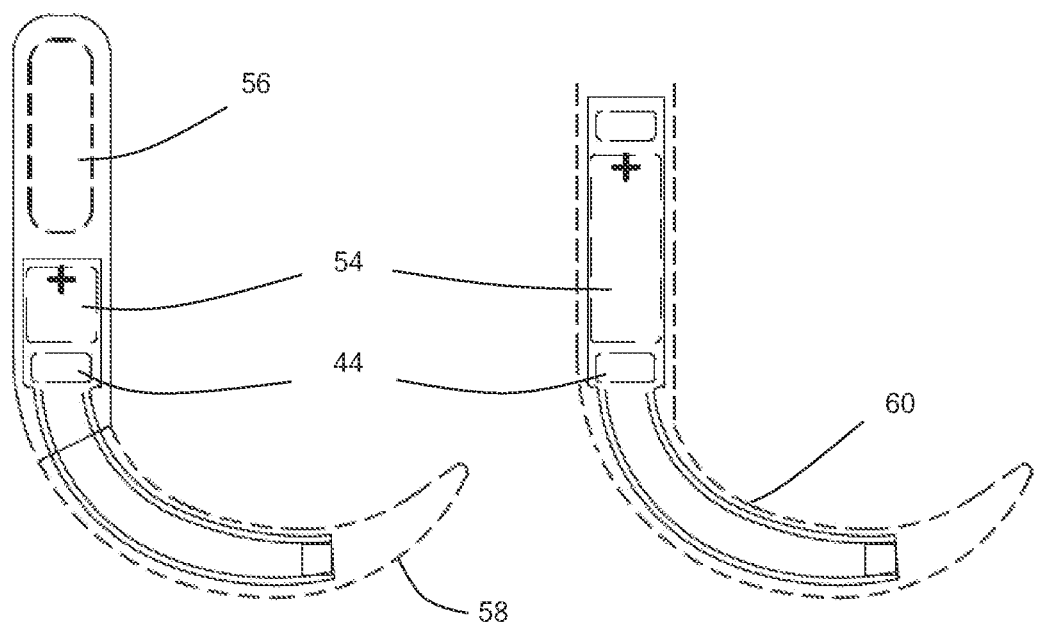
FIG. 2 is two side-on plan views of demountable sheaths that may be mounted onto a video laryngoscope.
Figure 3:
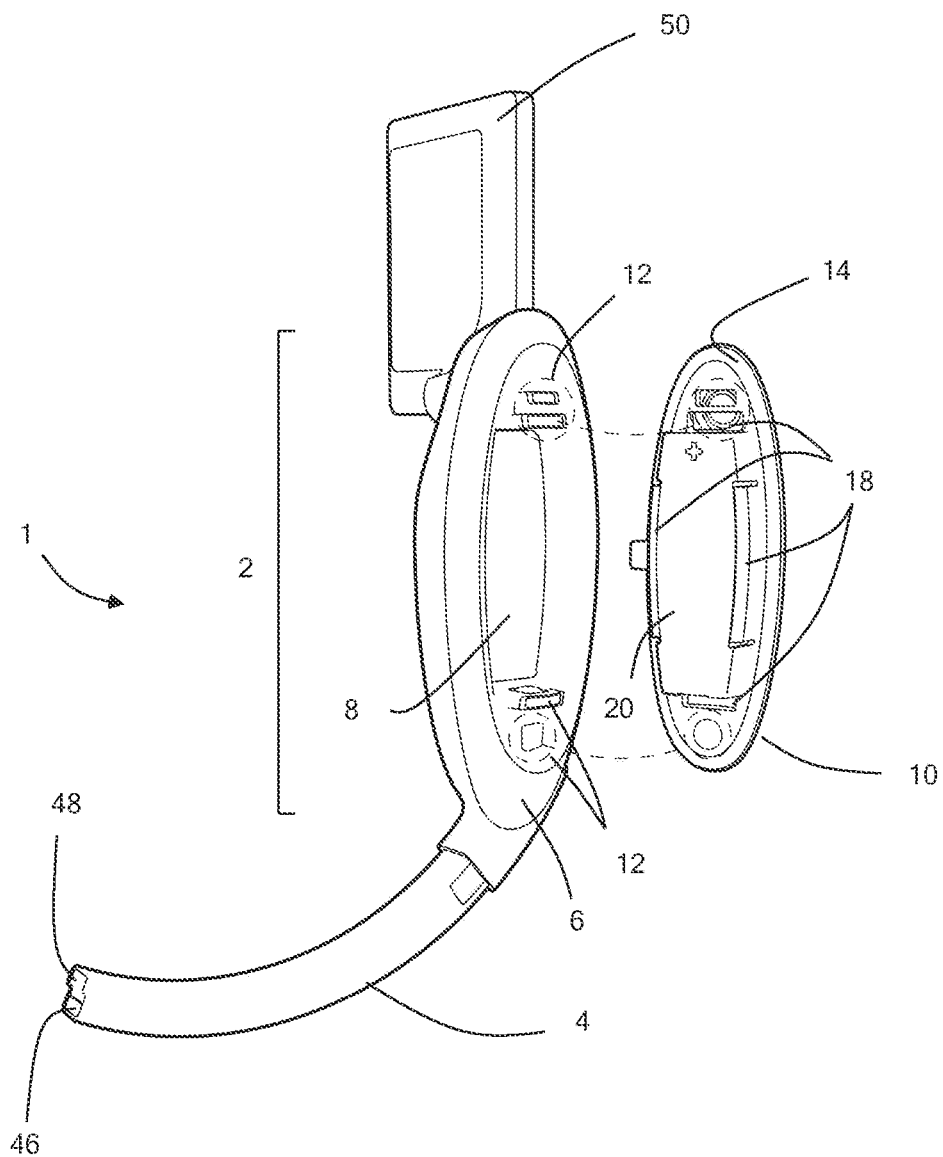
FIG. 3 is an exploded isometric view of a video laryngoscope with the battery pack removed.
Figure 4:
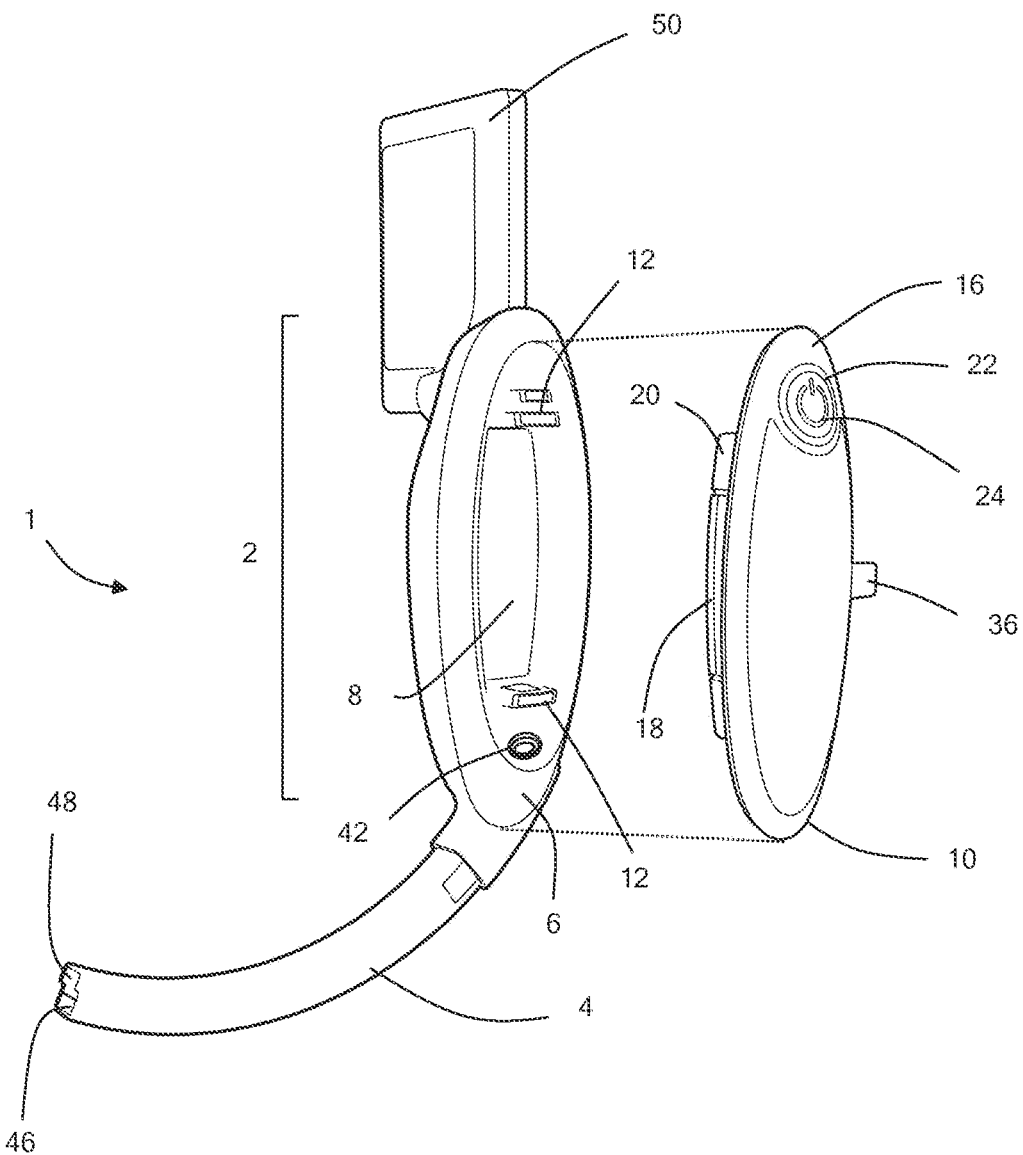
FIG. 4 is an exploded view of the video laryngoscope of FIG. 3 from an alternative angle.
Figure 5:
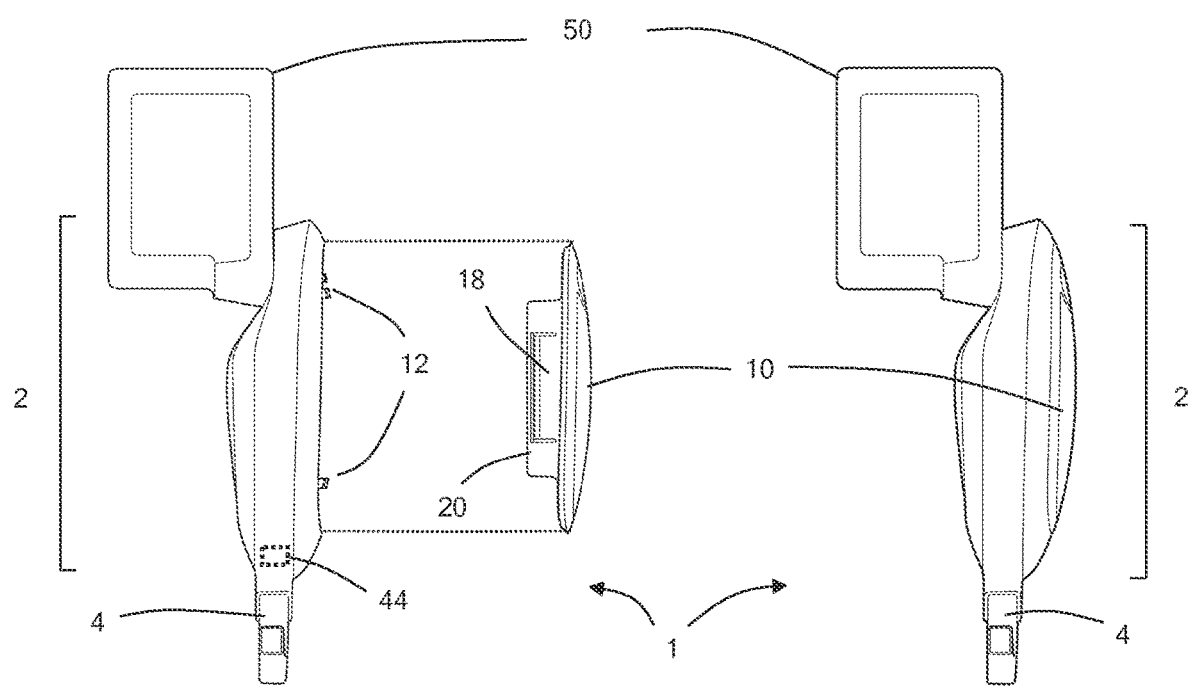
FIG. 5 is an exploded view from the front of the video laryngoscope of FIG. 3.
Figure 6A:
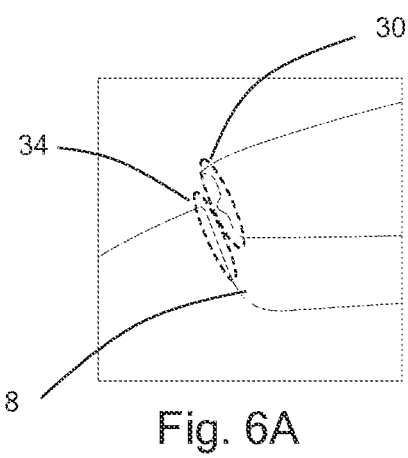
FIGS. 6A through 6D are sectional views through the electrical device before the battery pack is mounted (FIG. 6A), after the battery pack is mounted (FIG. 6B), with the battery pack and electrical device superimposed (FIG. 6C) and in expanded view (Fig.6D).
Figure 6B:
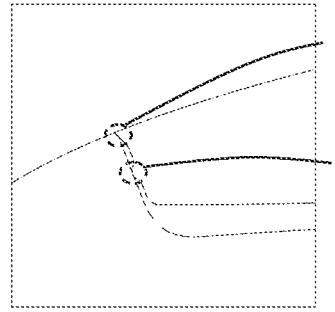
Figure 6C:
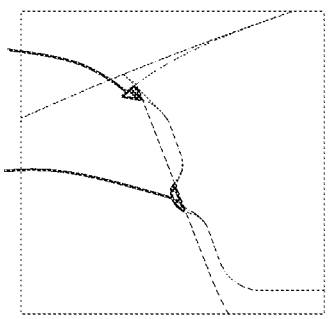
Figure 6D:
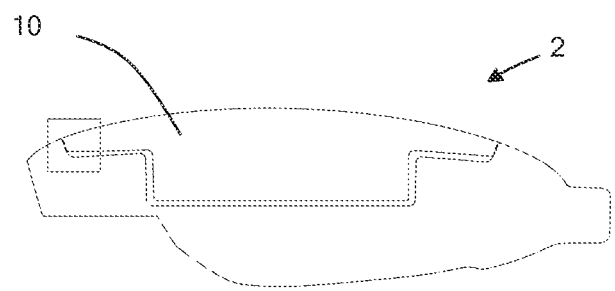

With reference to FIG. 1 a video laryngoscope 1 (being an example of an electrical device) comprises a body 2, and an arm 4 extending from the body. When prepared for use, a disposable rigid plastic sheath 58 or 60 is demountably retained on the arm, functioning as a laryngoscope blade.

The body of the video laryngoscope includes a processor unit 44 which comprises a memory unit and controls the functions of the video laryngoscope, including a light 46, a video camera 48, a video display 50 for displaying images from the video camera via a wired connection (acting as a connector) 52 and a battery 54 to provide power for the video laryngoscope. The surface of the body comprises an activation switch 22 and a light emitting diode 24 which functions as a display informing the user whether the video laryngoscope is activated.

The video laryngoscope further comprises an air gap 56 (acting as a low density portion) at the end of the body opposed to the arm.

In alternative embodiments the air gap may be replaced by low density foam or a recess in the surface of the body. Further alternatives may comprise more than one air gap.

A user begins operation of the device by pressing the activation switch. The device powers up, switching on the video camera, video screen and light. The processor reads the value stored in the memory unit. When the battery is new and unused, the value is a predetermined integer, such as 500. This value, or a number derived from it, is displayed on the screen as a numeral, or in another graphic format, such as a bar chart, pie chart, or any other graphical representation of available capacity.

As the device is used, the processor calculates the amount of usage. In some embodiments the processor simply determines the period of time for which the device is used. As the capacity of the battery is consumed, the value displayed on the screen is changed to reflect the reduced capacity, for example, the number 500 counts down. Periodically, the processor writes a new value to the memory unit, reflecting the reduced available rated capacity of the battery. This may be carried out each time the stored value should change, or may be carried out once when the device is powered down. The value stored in the memory unit can be updated quickly. As the activation switch is integral to the body of the video laryngoscope, a user cannot subvert the usage recording system by removing the memory unit to prevent the value stored on the memory unit from being updated.

The processor may change the stored value depending solely on the amount of time for which the electrical device has been used, or used in one or more s (e.g. modes in which the video screen is switched on in the case of a video laryngoscope). The processor may however take into account variations in power consumption by the device. More power will be consumed when a screen is on, for example, than when it is not. Thus, the processor may decrement the stored value more frequently in operating modes in which more power is consumed. The electrical device could include an ammeter but it is preferred to simply base changes to the value on measurements of the amount of time for which the device has been used, or used in specific operating modes, for simplicity. The processor may take into account environmental factors, such as temperature, measured by one or more sensors, such as a temperature sensor (e.g. a thermocouple), as such factors may affect battery life and/or power consumption.

Once the remaining available rated capacity of the battery reaches zero, or another threshold value as appropriate, the processor may cause the electronic device (or at least one function of the electronic device) to stop operating or to no longer start operating. The latter option may be preferable for a video laryngoscope used in an emergency environments as it could be dangerous for the device to stop functioning during an emergency procedure. It would be safer for it simply to not start functioning unless there was sufficient remaining available rated capacity to complete a procedure based on the known typical power consumption during that procedure. Before the device stops operating, or no longer starts operating, the device will typically output one or more audible or visual warnings.

As the stored value was initially chosen so that there was a high level of confidence that the capacity of the battery would not be exhausted before the remaining available rated capacity reached zero there will virtually always be some additional battery capacity available, although users should be discouraged from relying on or using this.

The device of the example embodiment also includes an override feature to enable a user to cause it to continue carrying out one or more functions, or to start carrying out one or more functions, even though the available rated capacity has dropped below the threshold. This may involve the user pressing a button but could involve another type of user interface. For example, the user may have to speak their name (which speech could be recorded), or to emit a loud noise at a loudspeaker of the device by shouting. Thus, an emergency override may be present but one which a user would not wish to use except in a genuine emergency.

The batteries cannot be accessed by a user and there is no recharging interface. Thus, there is a high level of confidence in the displayed available capacity.

Although the invention has been illustrated with the example embodiment of a video laryngoscope, the invention may also be employed with other types of electrical devices.

Second Embodiment

With reference to FIGS. 2 to 5 a video laryngoscope 1 (being an example of an electrical device) comprises a body 2, and an arm 4 extending from the body. When prepared for use, a disposable rigid plastic sheath (not shown) is demountably retained on the arm, functioning as a laryngoscope blade. The body portion comprises a first surface region 6, and a recess 8 for receiving a battery pack 10.

The body comprises electrical contacts 12 (functioning as an input interface) for receiving electrical power from the battery pack, located within the recess. The battery pack comprises a first major surface 14 and a second, opposed major surface 16. The first major surface comprises battery retaining formations 18 which retain a battery 20 and, when the battery pack is installed on the body the first major surface faces the body. The second major surface comprises an activation switch 22 and a light emitting diode 24 which functions as a display informing the user whether the video laryngoscope is activated. When the battery pack is installed on the body, the second major surface becomes a part of the outer surface of the laryngoscope, forming a grip for a user, along with the first surface region 6. The battery pack comprises electrical contacts 26 (functioning as an output interface) through which power can be transmitted to the electrical contacts on the body of the electrical device when the battery pack is fitted and the device is switched on.

The battery pack comprises a first seal 28 on a coupling surface 30 extending around the perimeter of the battery pack and a second seal 32 also located on the coupling surface. The seals are each formed as flexible polymeric ridges. Upon installation of the battery pack onto the body, the seals are compressed between the coupling surface and a cooperating surface 34 of the electrical device forming a waterproof seal around the perimeter of the battery pack.

The battery pack includes an RFID tag 38 including memory 40, and the body includes a solenoid coil 42 operable to inductively power the RFID tag (when the battery pack is fitted to the device), to read data from the RFID tag memory and to write data to the memory.

The body of the laryngoscope includes a processor 44 which controls the functions of the laryngoscope, including a light 46, a video camera 48, a video display 50 for displaying images from the video camera, and the solenoid coil.

When a battery pack is attached to the body (and so the device is in its assembled state) the body of the device is coated in a film of material, such as a plastic material to provide a smooth, water proof outer surface of the device. The device is now watertight and the battery pack may not be removed.

A user begins operation of the device by pressing the activation switch. The device powers up, switching on the video camera, video screen and light. The solenoid coil activates the RFID tag, reading the value stored in the memory. When the battery pack is new and unused, the value is a predetermined integer, such as 500. This value, or a number derived from it, is displayed on the screen as a numeral, or in another graphic format, such as a bar chart, pie chart, or any other graphical representation of available capacity.

As the device is used, the processor calculates the amount of usage. In some embodiments processor simply determines the period of time for which the device is used. As the capacity of the battery pack is consumed, the value displayed on the screen is changed to reflect the reduced capacity, for example, the number 500 counts down. Periodically, the processor causes the solenoid coil to power up the RFID tag and write a new value to the memory of the RFID tag, reflecting the reduced available rated capacity of the battery pack. This may be carried out each time the stored value should change, or may be carried out once when the device is powered down. The value stored on the RFID tag can be updated quickly. As the activation switch is integral to the battery pack, a user cannot subvert the usage recording system by removing the battery pack to prevent the value stored on the RFID tag from being updated.

The processor may change the stored value depending solely on the amount of time for which the electrical device has been used, or used in one or more operating modes (e.g. modes in which the video screen is switched on in the case of a video laryngoscope). The processor may however take into account variations in power consumption by the device. More power will be consumed when a screen is on, for example, than when it is not. Thus, the processor may decrement the stored value more frequently in operating modes in which more power is consumed. The electrical device could include an ammeter but it is preferred to simply base changes to the value on measurements of the amount of time for which the device has been used, or used in specific operating modes, for simplicity. The processor may take into account environmental factors, such as temperature, measured by one or more sensors, such as a temperature sensor (e.g. a thermocouple), as such factors may affect battery life and/or power consumption.

Once the remaining available rated capacity of the battery pack reaches zero, or another threshold value as appropriate, the processor may cause the electronic device (or at least one function of the electronic device) to stop operating or to no longer start operating. The latter option may be preferable for a video laryngoscope used in an emergency environments as it could be dangerous for the device to stop functioning during an emergency procedure. It would be safer for it simply to not start functioning unless there was sufficient remaining available rated capacity to complete a procedure based on the known typical power consumption during that procedure. Before the device stops operating, or no longer starts operating, the device will typically output one or more audible or visual warnings.

As the stored value was initially chosen so that there was a high level of confidence that the capacity of the battery pack would not be exhausted before the remaining available rated capacity reached zero there will virtually always be some additional battery capacity available, although users should be discouraged from relying on or using this.

The device of the example embodiment also includes an override feature to enable a user to cause it to continue carrying out one or more functions, or to start carrying out one or more functions, even though the available rated capacity has dropped below the threshold. This may involve the user pressing a button but could involve another type of user interface. For example, the user may have to speak their name (which speech could be recorded), or to emit a loud noise at a loudspeaker of the device by shouting. Thus, an emergency override may be present but one which a user would not wish to use except in a genuine emergency.

Once the battery pack has been exhausted the consumed battery pack cannot be replaced or recharged by the user. However, the electrical device may be returned to the manufacturer who may remove the film and remove the battery pack for recycling, recharging or reconditioning.

The memory of the RFID tag may store additional data, such as an identifier of the battery pack, or of an electrical device to which it is or has been fitted. Some or all of the data stored on the RFID tag, such as the stored value described above, may be encoded to prevent tampering.

Although the invention has been illustrated with the example embodiment of a video laryngoscope, the invention may also be employed with other types of electrical devices.

Further variation and modifications may be considered by one skilled in the art, within the scope of the invention herein disclosed.

The invention claimed is:

1. A method, comprising:
accessing a first value indicative of a remaining available rated capacity of a first battery pack of a video laryngoscope;
displaying the first value on a display screen of the video laryngoscope; updating the first value to reflect a first power consumption from the first battery pack resulting from operation of the video laryngoscope;
powering down the video laryngoscope;
accessing a second value indicative of a remaining available rated capacity of a second battery pack of the video laryngoscope in response to powering up the video laryngoscope after the powering down;
displaying the second value on the display screen of the video laryngoscope; and
updating the second value to reflect a second power consumption from the second battery pack resulting from additional operation of the video laryngoscope.

2. The method of claim 1, wherein powering down the video laryngoscope based on the updated first value comprises:
determining that the updated first value indicates the remaining available rated capacity of the first battery pack is below a predetermined threshold; and
powering down the video laryngoscope in response to determining that the updated first value is below the predetermined threshold.

3. The method of claim 1, wherein powering down the video laryngoscope deactivates one or more of the display screen, a video camera, and a light.

4. The method of claim 1, wherein updating the first value comprises writing the updated first value to a memory of the video laryngoscope.

5. The method of claim 1, wherein updating the first value to reflect the first power consumption from the first battery pack resulting from operation of the video laryngoscope comprises:
determining an operating mode of the video laryngoscope; and
updating the first value based on the first power consumption associated with the operating mode.

6. The method of claim 1, comprising outputting a sound or graphical indicator indicating that the remaining capacity determined from the updated first value is approaching zero.

7. The method of claim 1, wherein updating the first value comprises the first value based on a temperature as measured by a temperature sensor of the video laryngoscope.

8. The method of claim 1, wherein one or more batteries of the second battery pack have a different rated capacity than one or more batteries of the first battery pack.

9. A method, comprising:
accessing a first value stored in a memory of a video laryngoscope, wherein the first value is indicative of a remaining available rated capacity of a first battery pack of the video laryngoscope;
displaying a first graphical indicator of the first value on a display screen of the video laryngoscope;
powering down the video laryngoscope;
accessing a second value stored in the memory of the video laryngoscope, wherein the second value is indicative of a remaining available rated capacity of a second battery pack in response to powering up the video laryngoscope after the powering down; and
displaying a second graphical indicator of the second value on the display screen of the video laryngoscope.

10. The method of claim 9, wherein powering down the video laryngoscope is based on a user input.

11. The method of claim 9, wherein powering down the video laryngoscope is based on the first value.

12. The method of claim 9, comprising deactivating one or more components of the video laryngoscope based on the first value.

13. The method of claim 12, wherein the one or more components comprise the display screen, a video camera, and a light.

14. The method of claim 9, wherein the second battery pack comprises a different or recharged battery relative to the first battery back.

\* \* \* \* \*